United States Patent [19]

Scanlon et al.

[11] Patent Number: 5,880,277
[45] Date of Patent: *Mar. 9, 1999

[54] RIBOZYME CLEAVAGE OF 5α-REDUCTASE MRNA

[75] Inventors: Kevin J. Scanlon, Pasadena; Mohammed Kashani-Sabet, San Francisco, both of Calif.

[73] Assignees: City of Hope, Duarte; The Regents of the University of California, Oakland, both of Calif.

[*] Notice: This patent issued on a continued prosecution application filed under 37 CFR 1.53(d), and is subject to the twenty year patent term provisions of 35 U.S.C. 154(a)(2).

[21] Appl. No.: 895,235

[22] Filed: Jul. 16, 1997

Related U.S. Application Data

[63] Continuation of Ser. No. 747,508, Nov. 12, 1996, abandoned, which is a continuation of Ser. No. 275,877, Jul. 15, 1994, abandoned.

[51] Int. Cl.[6] ................................................. C07H 21/04
[52] U.S. Cl. ...................... 536/24.5; 536/23.1; 536/23.2; 435/6; 435/91.31; 435/375
[58] Field of Search .................. 435/6, 91.31, 172.3, 435/320.1, 325, 375; 536/23.1, 23.2, 24.5; 514/44

[56] References Cited

PUBLICATIONS

Rossi et al. AIDS Res. & Human Retrovirus. 8:183, (1992).
Stull et al. Pharm. Res. 12:465, (1995).
Andersson, S. et al., *Proc. Natl. Acad. Sci. USA*, 87:3640–3644 (May 1990).
Bratty, J. et al., *Biochimica et Biophysica Acta.*, 1216:345–359 (1993).
Friedmann, T., *Science*, 244:1275–1281 (Jun. 1989).
Gao, L. et al., *Human Gene Therapy*, 4:17–24 (1993).
Gaston, K. et al., *Nucleic Acids Research*, 20 (No. 23):6297–6301 (1992).
Haseloff, J. et al., *Nature*, 334:585–591 (Aug. 1988).
Kashani–Sabet, M. et al., *Antisense Research and Development*, 2:3–15 (1992).
Labrie, F. et al., *Endocrinology*, 131 (No. 3):1571–1573 (1992).
Philip, R. et al., *Molecular and Cellular Biology*, 14 (No. 4):2411–2418 (Apr. 1994).
Synder, D. et al., *Blood*, 82 (No. 2):600–605 (Jul. 1993).
Taylor, N. et al., *Nucleic Acids Research*, 20 (No. 17):4559–4565 (1992).
Zhu, N. et al., *Science*, 261:209–211 (Jul. 1993).
Harris, G., et al., *Proc. Natl. Acad. Sci. USA*, 89:10787–10791 (1992).
Suwaya, M., *Dermatology, Progress & Perspectives: Proceedings of the 18th World Congress of Dermatology*, pp. 202–203 (1992).
McConnell, J., et al., *J. Clin. Endocrinol. Metab.*, 74(No. 3):505–508 (1992).
Andersson, S., et al., *Nature*, 354:159–161 (1991).
Cunha, G., et al., *Endocr. Rev.*, 8(No. 3):338–362 (1987).

(List continued on next page.)

*Primary Examiner*—John L. LeGuyader
*Attorney, Agent, or Firm*—Rothwell Figg Ernst & Kurz

[57] ABSTRACT

The steroid enzyme 5α-reductase is responsible for the conversion of testosterone to the more-potent androgen dihydrotestosterone (DHT). The catalytic cleavage of nucleic acid encoding 5α-reductase by a ribozyme which selectively recognizes such nucleic acid reduces the level of expression of 5α-reductase by mammalian cells including human cells treated with such ribozyme. The reduction of nucleic acid (e.g. mRNA) levels leads to a corresponding reduction of enzyme levels and dihydrotestosterone levels in surrounding tissues, thus providing a therapeutic effect. The transformation of 5α-reductase producing cells with an expression vector containing a structural gene for a ribozyme is shown to decrease 5α-reductase expression. Pharmaceutical compositions and methods useful for topically administering effective amounts of such a ribozyme to hair follicle cells also are exemplified.

2 Claims, 3 Drawing Sheets

PUBLICATIONS

Mooradian, A., et al., *Endocr. Rev.*, 8(No. 1):1–28 (1987).

Cech, T., et al., *Ann. Rev. Biochem.*, 55:599–629 (1986).

Cunliffe, W., et al., *The Lancet*, 1:685–687 (1969).

Hamilton, J., *Am. J. Anat.*, 71:451–480 (1942).

M. Kashani–Sabet et al., "Application of ribozymes to cancer gene therapy," *Cancer Gene Therapy*, vol. 2, No. 3, 1995, pp. 213–223.

K. Scanlon et al., "Ribozyme–mediated reversal of the multidrug–resistant phenotype," *Proc. Natl. Acad. Sci. USA*, vol. 91, pp. 11123–11127, Nov. 1994.

H. Kobayashi et al., "Reversal of Drug Sensitivity in Multidrug–Resistant Tumor Cells by an MDRI (PGY1) Ribozyme," *Cancer Research*, 54:1271–1275, Mar. 1, 1994.

J. Ohkawa et al., "Importance of independence in ribozyme reactions: Kinetic behavior of trimmed and of simply connected multiple ribozymes with potential activity against human immunodeficiency virus," *Proc. Natl. Acad. Sci. USA*, vol. 90, pp. 11302–11306, Dec. 1993.

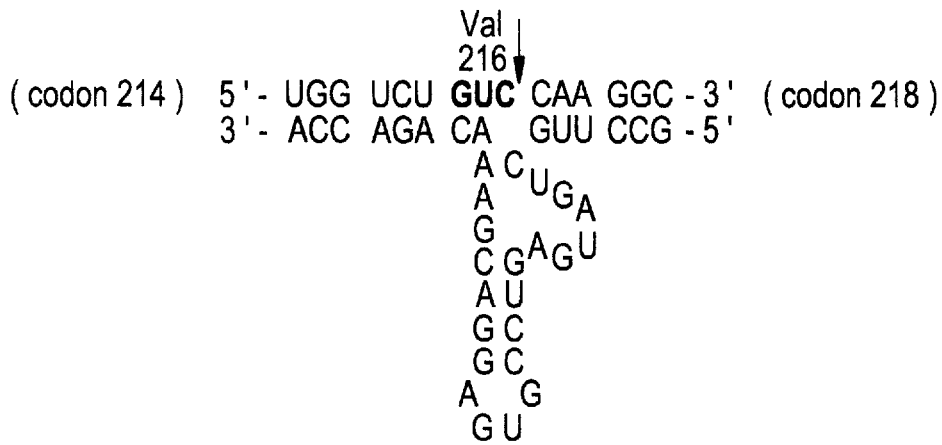
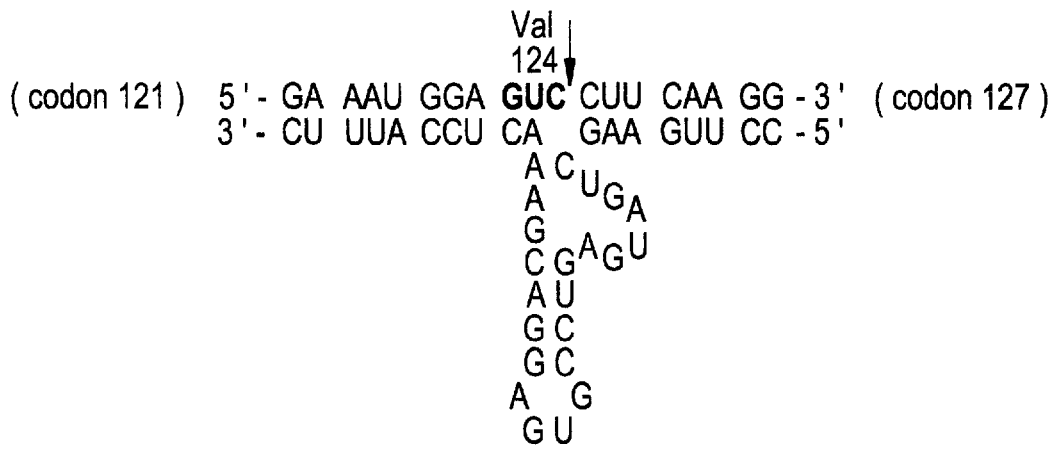

pHβ - Apr 1
(5α reductase Ribozyme)

RIBOZYME CLEAVAGE OF 5α-REDUCTASE MRNA

This is a continuation of application Ser. No. 08/747,508 filed Nov. 12, 1996, which is a continuation of Ser. No. 08/275,877, filed Jul. 15, 1994 (abandoned).

BACKGROUND OF THE INVENTION

1. Technical Field

The present invention relates to the cleavage of mRNA directing the expression of the enzyme steroid 5α-reductase in mammalian cells, including human cells. More specifically, the present invention provides ribozymes capable of selectively cleaving such mRNA, thereby advantageously reducing the expression of 5α-reductase by cells exposed to such a ribozyme. The invention also provides methods and compositions for administering such ribozymes to cells, including methods and compositions for topically administering a 5α-reductase-mRNA-specific ribozyme to, inter alia, hair follicle cells for the treatment of androgenic alopecia.

2. Description of the Background Art

The microsomal enzyme steroid 5α-reductase (EC1.3.99.5) catalyzes the conversion of 4-ene-3-keto-steroids to the corresponding 5α-dihydro-3-keto steroids in human and other mammalian tissues. The conversion of testosterone to the more-potent androgen dihydrotestosterone ("DHT") is one of the best-characterized and best-known roles of this enzyme. DHT is considered to be the most potent androgen and to be responsible for differentiation of the male external genitalia and prostate as well as for virilization at puberty. See Labrie et al., Endocrinology 131:3, 1571–1573 (1992).

Of the several organs that produce androgens, the testes produce these hormones in the greatest amounts. Centers in the brain exert primary control over the level of androgen production and, as described in greater detail below, numerous physical manifestations and disease states result when ineffective production control results in excessive androgen hormone production.

The enzyme 5=-reductase plays a major role in a variety of androgen-specific diseases, dysfunctions and physical conditions including but not limited to prostate cancer, benign prostatic hyperplasia, acne, seborrhea, hirsutism and androgenic alopecia including male pattern baldness. A variety of chemical inhibitors of this enzyme have been proposed for various therapeutic uses. See for example McConnell et al., J. Clin. Endocrinol. Metab. 74:505–508, which describes the use of finasteride for suppressing prostatic DHT in men with benign prostatic hyperplasia. The development of inhibitors of 5α-reductase has been hampered, however, by the absence of sufficient knowledge of the structure of the protein and by the very low levels of expression even in androgen-responsive tissues. See Andersson, S. et al., PNAS USA 87:3640–3644 (May, 1990). Moreover, in the case of finasteride, development of impotence is an undesirable side effect of this agent. Thus, there remains a need for improved effective and specific means for suppressing the production of DHT in patients in need thereof.

Benign prostatic hypertrophy (BPH) is a common problem in elderly males due to increased conversion of testosterone to DHT via increased activity of 5-α reductase, with significant clinical morbidity including obstruction, urinary retention, and difficulty in initiating or terminating urinary stream. Management of BPH is predominantly surgical with the risk of inherent complications. Recently, finasteride, a specific inhibitor of 5α-reductase, has shown some promise in the treatment of BPH despite the development of impotence in some patients (McConnell et al. as above). Therefore, development of an improved effective and specific means for suppressing the production of DHT via the 5-reductase pathway will find utility beyond the treatment of androgenic alopecia.

It is well established that, in androgenic alopecia (including male pattern baldness), an accumulation of androgens, especially DHT, in hair follicle cells plays a significant role. See Hamilton, J. B., Am. J. Anat., 71:451–480 (1942); Mooradian et al., Endocr. Rev., 8:1–28 (1987); Cunha et al., Endocr. Rev., 8:338–362 (1987). Testosterone circulating in the bloodstream serves as a prohormone for the more-active DHT in certain tissues. Testosterone is converted to the more-potent androgen DHT in the epidermis (Harris et al., Proc. Natl. Acad. Sci. USA 89:10787–10791 (1992)), this conversion being catalyzed by the 5α-reductase enzyme. Male pattern baldness is characterized by the shrinkage of hair follicles on the crown of the head, ultimately leading to such follicles becoming dormant. Such shrinkage of hair follicles is largely due to the action of testosterone and DHT on the hair follicle cells. Individuals showing male pattern baldness begin to lose their hair early in life—often in their twenties—and may employ a variety of techniques with hopes of reversing the condition, often at great expense but with minimal effect.

It had been postulated that the presence of accumulations of DHT in the skin gives rise to the symptoms of both acne and androgenic alopecia including male pattern baldness. The presence of increased levels of 5α-reductase in hair follicles of patients, both male and female, exhibiting androgenic alopecia has been demonstrated. M. E. Sawaya reported (Dermatology, Progress & Perspectives, Proceedings of the 18th World Congress of Dermatology, pp. 202–203 (1992), Parthenon Pub. Group) that frontal follicles of women exhibiting androgenic alopecia contained almost twice the 5α-reductase level of occipital follicles, and that frontal follicles of men exhibiting androgenic alopecia contained more than twice the 5α-reductase level of occipital follicles. Thus, there is today little question that the conversion of testosterone to DHT, catalyzed by the enzyme 5α-reductase, plays an important role in androgenic alopecia.

With respect to acne, sebum secretion is on average higher in patients with acne vulgaris than their normal counterparts. Therefore, compounds which reduce sebum production have therapeutic potential. Among such agents are anti-androgens, including 5α-reductase inhibitors (Cuncliffe and Schuster, Lancet, 1:685–687 (1969)).

Among the several functions of RNA within cells is its role of enzymatic catalysis. Ribozymes are catalytic RNA's that have the capacity to specifically base-pair with, cleave and thus functionally destroy a an RNA sequence. See, generally, Cech and Bass, Ann. Rev. Biochem. 55:599–629 (1986). In nature, these RNA catalysts function in cis, cleaving a portion of the same RNA strand upon which they reside. The isolation of the catalytic portions of such RNA's into discreet molecules, or "trans-acting" ribozymes, however, has provided useful reagents having riboendonuclease activity. See Haseloff & Gerlach, Nature 334:585–591 (1988).

The class of "hammerhead" ribozymes, for example, comprises such trans-acting reagents. Hammerhead ribozymes cleave an exogenous RNA template immediately 3' to a GUX sequence (wherein X is C, A or U). Hammerhead ribozymes are comprised of a conserved catalytic core flanked by sequences complementary to the desired target RNA sequence to confer target specificity (Haseloff et al., supra.). Even more recently, the ability to engineer ribozymes in a variety of ways, for improved cleavage specificity and enhanced catalytic turnover, for example, has been documented. Thus, catalytic RNA's (which may also contain one or more deoxyribonucleotide bases), generically referred to herein as "ribozymes," which are capable of site-specific cleavage of exogenous RNA (and sometimes DNA) strands present an important mechanism for the modulation of gene expression in mammalian cells.

Two human 5α-reductase enzymes have been identified, and their genes have been isolated and sequenced. The cDNA and amino acid sequences of human type I 5α-reductase appears in Andersson, S. et al., supra, which publication indicated that the amino acid sequence has been deposited in the GenBank data base under accession no. M32313. Andersson et al. reported the discovery of a second human (type II) 5α-reductase in Nature, 354:159–161 (1991), which, unlike the type I enzyme, is the major 5α-reductase found in prostatic tissues and is sensitive to finasteride. The isolation and structural characterization of the human type II 5α-reductase gene, including its sequence, were reported by Labrie et al. in Endocrinology 131:3, pp. 1571–1573 (1992).

Accordingly, it is an object of the present invention to provide a means for reducing the production or accumulation of DHT in mammalian tissues, including human tissues.

Another object of the present invention is to reduce the production or accumulation of DHT in tissues, especially epidermal tissue, by reducing the expression of the microsomal steroid enzyme 5α-reductase in epidermal tissue.

An additional object of the invention is to provide a pharmaceutical composition for topical application which contains a ribozyme capable of cleaving mRNA coding for 5α-reductase.

Yet another object of the invention is to provide a method for treating androgenic alopecia by the topical application of a ribozyme capable of cleaving mRNA coding for 5α-reductase.

A still further object of the invention is to provide reagents useful for the in vitro study of the biosynthesis of mammalian 5α-reductase enzymes, including the human type I and type II enzymes. Such reagents contain amounts of a 5α-reductase-mRNA-specific ribozyme effective to reduce or halt entirely the production of 5α-reductase by cells exposed to them.

BRIEF DESCRIPTION OF THE DRAWINGS

FIG. 1 illustrates the ribonucleotide base sequence and secondary structure of a Type I 5α-reductase ribozyme in accordance with the present invention (SEQ ID NO:1 and SEQ ID NO:2).

FIG. 2 illustrates the ribonucleotide base sequence and secondary structure of a Type II 5α-reductase ribozyme in accordance with the present invention (SEQ ID NO:3 and SEQ ID NO:4).

SUMMARY OF THE INVENTION

Figure 3:
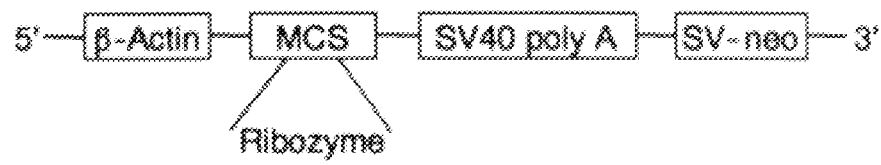
FIG. 3 illustrates an expression vector, pHβ-Apr1, containing DNA encoding the ribozyme of FIG. 1 for constitutive expression under the control of a β-actin promoter.

The foregoing and other objects are attained in accordance with the present invention which in one aspect provides a method for reducing the production of 5α-reductase by mammalian (including human) cells by administering to a 5α-reductase-producing cell a ribozyme capable of cleaving mRNA coding for said 5α-reductase. In preferred embodiments, the 5α-reductase is human type I or type II 5α-reductase. The method can be carried out in vitro or in vivo via, for example, (1) the topical application of the ribozyme to, e.g., epidermal cells including hair follicle cells of the scalp, or (2) by transforming a 5α-reductase producing mammalian cell with a gene encoding the ribozyme under control of expression signals which will direct the expression of said ribozyme, optionally under the control of a tissue-specific promotor.

In other aspects, the invention provides a pharmaceutical composition for topical application to the situs of disease that is associated with the action of DHT, such as the scalp (androgenic alopecia) or facial skin (acne) comprising an effective amount of a ribozyme capable of cleaving mRNA coding for 5α-reductase, along with a pharmaceutically-acceptable carriers and adjuvants for promoting the uptake of such ribozyme by 5α-reductase producing cells at the situs.

The invention also provides a method for treating androgenic alopecia, including male pattern baldness, by applying to the situs a composition comprising an effective amount of a ribozyme capable of cleaving mRNA coding for 5α-reductase.

The present invention also includes within its scope ribozymes per se which are capable of selectively hybridizing to and cleaving nucleic acid (DNA or RNA) encoding 5α-reductase, as well as the combination of such a ribozyme bound to such a nucleic acid.

DETAILED DESCRIPTION OF THE PREFERRED EMBODIMENTS

The steroid dihydrotestosterone (DHT) is considered to play an important role in a variety of androgen-mediated diseases and conditions, including prostate cancer, benign prostatic hyperplasia, acne, seborrhea, hirsutism and androgenic alopecia including male pattern baldness. The biosynthetic pathway of DHT includes the 5α-reductase-mediated conversion of testosterone to DHT. This conversion (and the presence of increased amounts of 5α-reductase) has been observed to occur in epidermal tissues, and specifically at the epidermal situs of patients with acne and androgenic alopecia.

The present invention provides, among other features, a novel approach to the reduction of DHT in epidermal tissues. The invention provides, in its various aspects, methods and compositions for reducing or completely halting the expression of 5α-reductase at the molecular genetic level. The application to epidermal cells of a ribozyme capable of specifically cleaving mRNA coding for 5α-reductase reduces or halts the expression of this enzyme, thereby reducing or halting the conversion of testosterone to the more-potent androgen DHT in surrounding tissues. The reduction of DHT levels provides a therapeutic effect for conditions caused or exacerbated by DHT.

A number of classes of catalytic RNAs (ribozymes) have been described in the literature, and the present invention is not limited to any one class of ribozyme. In a preferred aspect, however, the ribozymes of the present invention are "hammerhead" ribozymes. Such ribozymes have a hybridizing region (conferring the desired specificity) comprising one or more arms formed of single stranded RNA having a sequence complementary to at least part of a target nucleic acid, such as mRNA. The hybridizing (or "anti-sense") regions comprise segments of RNA typically containing at least 8 nucleotides, typically 9 to 12 nucleotides. A conserved catalytic core region is capable of cleaving the target RNA.

The preferred ribozymes of the present invention cleave target RNA which contains the sequence $X_1UX_2$, where $X_2$ is adenine, cytosine or uracil and U is uracil. Preferably, $X_1$ is guanidine, and $X_1UX_2$ is GUC or GUA. The anti-sense arms of the ribozyme can be synthesized to be complementary to, and thus hybridizable to, the RNA on the target 5α-reductase mRNA sequence flanking the chosen $X_1UX_2$ sequence. Upon hybridization of the anti-sense regions of the ribozyme to the target RNA sequence flanking the $X_1UX_2$ sequence, the catalytic region of the ribozyme cleaves the target RNA within the $X_1UX_2$ sequence. RNA cleavage is facilitated in vitro in the presence of magnesium or another divalent cation at a pH of approximately 8.0.

In one embodiment of the invention, there is provided a hammerhead ribozyme as seen in FIG. 1. This ribozyme comprises a catalytic region that recognizes a GUC sequence within the mRNA of human Type I 5α-reductase, cleaving 3' to the cytosine. The ribozyme also comprises two anti-sense regions corresponding to the base sequence of the 5α-reductase mRNA upstream and downstream of the targeted GUC cleavage site.

FIG. 2 illustrates a hammerhead ribozyme capable of cleaving the mRNA of human Type II 5α-reductase. This ribozyme, too, contains a catalytic core region capable of cleaving a target nucleic acid strand and specificity-imparting anti-sense regions corresponding to the sequence of the target mRNA.

It will be readily apparent that the sequences of the ribozymes of FIGS. 1 and 2 can be modified without departing from the invention. The catalytic regions can be targeted to any $X_1UX_2$ sequence within the 5α-reductase mRNA, with the proviso that the $X_1UX_2$ sequence should be selected so as to result in the cleavage of the mRNA into one or more RNA strands that are incapable of serving as template(s) for the translation of a functional 5α-reductase molecule. Anti-sense regions capable of effectively bonding to bases (preferably 8 to 12 bases) upstream and downstream from the selected $X_1UX_2$ sequence will be selected based upon knowledge of the mRNA sequence.

The ribozymes can be further modified to include nuclease-resistant RNA bases. These modifications include the use of phosphorothioate derivatives of nucleotides (reviewed in Bratty et al., Biochim. Biophys. Acta, 1216:345–359 (1993)) to confer resistance to nucleases which degrade the ribozyme. The phosphorothioate group is introduced into an oligonucleotide using RNA or DNA polymerase and the corresponding nucleoside α-thiotriphosphate. Alternatively, the phosphorothioate group is inserted at specific positions in an oligomer as a phosphoramidite during chemical synthesis.

The ribozyme also can be synthesized in the form of a chimeric ribozyme containing deoxyribonucleotide as well as ribonucleotide bases. These chimeric ribozymes have been shown to have increased cellular stability while maintaining efficient cleavage properties. The chemistry of chimeric (DNA-containing) ribozymes (also known as "nucleozymes") is reviewed in Bratty et al. supra. For original article, see Taylor et al., Nucleic Acids Res., 20:4559–4565 (1992).

The invention includes within its scope methods and compositions for applying a 5α-reductase specific ribozyme to the surface of a 5α-reductase-producing cell such that the ribozyme effectively enters the cell and cleaves 5α-reductase specific nucleic acid. In vitro, a solution containing the ribozyme is applied to 5α-reductase cells in cell culture. Compositions for topical application to the scalp, for example, are preferably formulated as liquids for ease of application to the situs and to promote penetration to the cellular level of involved epidermal tissue. Viscous liquids, creams, ointments and the like may be used for prolonged contact at the desired site.

Pharmaceutically-acceptable compositions for topical application include creams, lotions, solutions, ointments and shampoos. Such compositions are per se known.

Inasmuch as ribozymes act intracellularly, the uptake of ribozymes by the targeted cells is an important consideration and should be optimized. Direct cellular uptake of oligonucleotides (whether they are composed of DNA or RNA or both) per se presently is considered to be a less-preferred method of delivery because, in the case of ribozymes and antisense molecules, direct administration of oligonucleotides carries with it the concomitant problem of attack and digestion by cellular nucleases, such as the RNAses.

One preferred mode of administration of 5α-reductase ribozymes takes advantage of known vectors to facilitate the delivery of a gene coding for the desired ribozyme sequence such that it will be expressed by the desired target cells. Such vectors include plasmids, viruses (such as adenoviruses, retroviruses, and adeno-associated viruses) and liposomes (reviewed in Friedmann, Science, 244:1275–1281 (1989)) and modifications therein (e.g., polylysine-modified adenoviruses [Gao et al., Human Gene Therapy, 4:17–24 (1993)], cationic liposomes [Zhu et al., Science, 261:209–211 (1993)], and modified adeno-associated virus plasmids encased in liposomes [Philip et al., Mol. Cell. Biol., 14:2411–2418 (1994)]). Expression of ribozyme RNA is driven by genetic elements such as the β-actin, cytomegalovirus (CMV), and metallothionein promoters as well as more tissue restrictive elements such as various keratin gene promoters, the prostatic specific antigen promoter, and the tyrosinase promoter. The use of these latter tissue-specific promoters is preferred in certain aspects of the invention.

Example 1 herein illustrates the successful transfection of 5α-reductase producing cells with an expression vector containing a structural gene coding for the ribozyme of FIG. 2 operatively linked to a β-actin promoter.

The ribozymes of the present invention may be prepared by methods known per se in the art for the synthesis of RNA molecules. In particular, the ribozymes of the invention may be prepared from a corresponding DNA sequence (DNA which on transcription yields a ribozyme, and which may be synthesized according to methods known per se in the art for the synthesis of DNA) operably linked to a promoter. A DNA sequence corresponding to a ribozyme of the present invention may be ligated into a DNA transfer vector, such as plasmid, bacteriophage DNA, viral DNA, or liposomes. Prokaryotic or eukaryotic cells (including mammalian and plant cells) may then be transfected with an appropriate transfer vector containing genetic material corresponding to the ribozyme in accordance with the present invention, operably linked to a promoter, such that the ribozyme is transcribed in the host cell. Ribozymes may be directly transcribed from a transfer vector, or, alternatively, may be transcribed as part of a larger RNA molecule which then may be cleaved to produce the desired ribozyme molecule. While the present application describes various methods of transforming cells so as to produce the desired ribozyme, those skilled in the general field of non-native (recombinant) gene expression in mammalian cells will apply per se known techniques to provide additional means and methods for providing or optimizing ribozyme expression in 5α-reductase producing cells.

EXAMPLE 1

Figure 4:
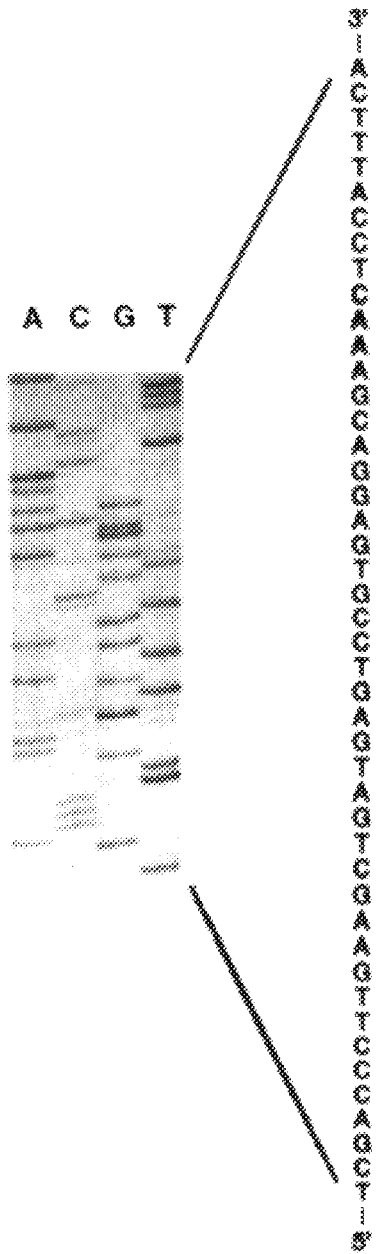
FIG. 4 illustrates the results of dideoxynucleotide DNA sequencing which confirmed the sequence of the expression vector of FIG. 3. (SEQ ID NO:5)

The sequences of two hammerhead ribozymes designed to cleave 5α-reductase mRNA are depicted in FIGS. 1 and 2, along with the complementary sequences of 5α-reductase RNAs. FIG. 1 shows the type I ribozyme, with cleavage of type I 5α-reductase mRNA occurring immediately 3' to the GUC position at codon 216. FIG. 2 shows the type II ribozyme, with the cleavage site 3' to the GUC sequence at codon 124. DNA encoding the type II 5α-reductase ribozyme was cloned into the pHβApr-1neo expression plasmid, which uses the β-actin gene promoter to constitutively express ribozyme RNA and contains the neomycin resistance gene (FIG. 3). The sequence of the DNA encoding the ribozyme in the plasmid was confirmed by dideoxy-nucleotide sequencing of the plasmid (FIG. 4). The resultant plasmid, pHβ 5α-reductase ribozyme, was transfected into A2780 human ovarian carcinoma cells which express the 5α-reductase gene. Transfected cells were grown in the presence of the neomycin analog geneticin in order to select a neomycin-resistant population. Six clones were selected and assayed for 5α-reductase ribozyme expression. RNA was isolated from the ribozyme-containing clones and subjected to Polymerase Chain Reaction (PCR) analysis to amplify the ribozyme sequence using primers specific for the 5α-reductase ribozyme. The blots were then hybridized with a labeled probe to detect expression of the ribozyme.

Figure 5:
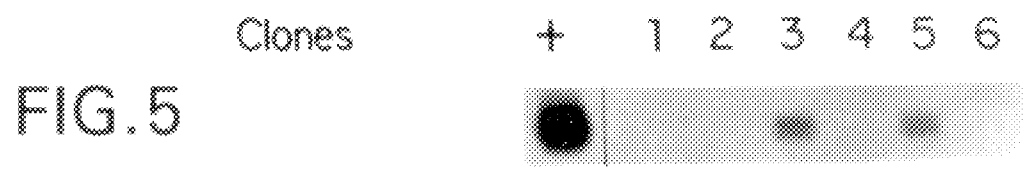
FIG. 5 illustrates the detection of ribozyme expression in transformed cells.
Figure 6:
FIG. 6 illustrates decreased expression of 5α-reductase by transformed cells.

FIG. 5 demonstrates such expression in lanes 3 and 5. These clones were then propagated in tissue culture and assayed for 5α-reductase gene expression. Northern analysis of RNA from these cell lines in FIG. 6 revealed that ribozyme-containing colonies in lanes 2 and 3 had decreased expression of 5α-reductase when compared to control A2780 cells which were transfected with the pHβ-Apr-1neo vector lacking the ribozyme sequences. There was no significant change in gene expression of phosphoglycerate kinase (PGK), used as a control gene, in ribozyme-transfected cells.

These results indicate that the 5α-reductase ribozyme, when stably expressed in the A2780 cell line, acted to inhibit 5α-reductase gene expression. Similar results were obtained by transfecting the ribozyme-containing plasmid into MCF-7 human breast carcinoma cells.

We claim:

1. The ribozyme of FIG. 1 (SEQ ID NO:1 and SEQ ID NO:2).

2. The ribozyme of FIG. 2 (SEQ ID NO:3 and SEQ ID NO:4).

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: YES ( x i ) SEQUENCE DESCRIPTION: SEQ ID NO:1:

UGGUCUGUCC AAGGC                                                              1 5

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: NO ( x i ) SEQUENCE DESCRIPTION: SEQ ID NO:2:

GCCUUGCUGA UGAGUCCGUG AGGACGAAAC AGACCA 36

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: RNA (genomic)

(iii) HYPOTHETICAL: NO (iv) ANTI-SENSE: YES (xi) SEQUENCE DESCRIPTION: SEQ ID NO:3:

GAAAUGGAGU CCUUCAAGG 19

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:4:

CCUUGAAGCU GAUGAGUCCG UGAGGACGAA ACUCCAUUUC 40

(2) INFORMATION FOR SEQ ID NO:5:

(i) SEQUENCE CHARACTERISTICS:
        (A) LENGTH: 46 base pairs
        (B) TYPE: nucleic acid
        (C) STRANDEDNESS: both
        (D) TOPOLOGY: linear (ii) MOLECULE TYPE: DNA (genomic)

(iii) HYPOTHETICAL: NO (xi) SEQUENCE DESCRIPTION: SEQ ID NO:5:

TCGACCCTTG AAGCTGATGA GTCCGTGAGG ACGAAACTCC ATTTCA 46